United States Patent
Nappa et al.

(10) Patent No.: US 8,263,817 B2
(45) Date of Patent: Sep. 11, 2012

(54) SYNTHESIS OF 1234YF BY SELECTIVE DEHYDROCHLORINATION OF 244BB

(75) Inventors: Mario Joseph Nappa, Newark, DE (US); Robert D. Lousenberg, Wilmington, DE (US); Andrew Jackson, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/172,987

(22) Filed: Jun. 30, 2011

(65) Prior Publication Data

US 2012/0172638 A1     Jul. 5, 2012

Related U.S. Application Data

(60) Provisional application No. 61/361,713, filed on Jul. 6, 2010.

(51) Int. Cl.
    *C07C 17/25*     (2006.01)
(52) U.S. Cl. .................... 570/157; 570/156
(58) Field of Classification Search .............. None
See application file for complete search history.

(56) References Cited

U.S. PATENT DOCUMENTS

| | | | |
|---|---|---|---|
| 3,413,363 A | 11/1968 | Pindzola | |
| 6,359,183 B1* | 3/2002 | Christoph et al. | 570/156 |
| 2006/0106263 A1 | 5/2006 | Miller et al. | |
| 2007/0197842 A1 | 8/2007 | Mukhopadhyay et al. | |
| 2009/0030247 A1 | 1/2009 | Johnson et al. | |
| 2009/0127496 A1* | 5/2009 | Rao et al. | 252/67 |
| 2009/0149680 A1 | 6/2009 | Wang et al. | |
| 2010/0185029 A1* | 7/2010 | Elsheikh et al. | 570/157 |

FOREIGN PATENT DOCUMENTS

| | | |
|---|---|---|
| EP | 0407711 A1 | 1/1991 |
| WO | 2008075017 A1 | 6/2008 |

OTHER PUBLICATIONS

Currie, Susan, International Search Report, PCT/US2011/042984, Filing Date Jul. 6, 2011.

* cited by examiner

*Primary Examiner* — Sudhakar Katakam

(57) ABSTRACT

Disclosed is a process for the manufacture of 2,3,3,3-tetrafluoropropene comprising: (a) contacting 1,1,1,2,tetrafluoro-2-chloropropane with a catalyst comprised of chromium (III) oxide, and at least 1% of an alkali metal, to produce a product mixture comprising 2,3,3,3-tetrafluoropropene; and (b) recovering said 2,3,3,3-tetrafluoropropene from the product mixture produced in step (a) above.

7 Claims, No Drawings

SYNTHESIS OF 1234YF BY SELECTIVE DEHYDROCHLORINATION OF 244BB

CROSS REFERENCE TO RELATED APPLICATIONS

This application claims priority to U.S. Provisional application 61/361,713, filed Jul. 6, 2010.

BACKGROUND INFORMATION

1. Field of the Disclosure

This disclosure relates in general to methods of synthesis of fluorinated olefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential.

There is also considerable interest in developing new refrigerants with reduced global warming potential for the mobile air-conditioning market.

HFC-1234yf ($CF_3CF=CH_2$) and HFC-1234ze ($CF_3CH=CHF$), both having zero ozone depletion and low global warming potential, have been identified as potential refrigerants. U. S. Patent Publication No. 2006/0106263 A1 discloses the production of HFC-1234yf by a catalytic vapor phase dehydrofluorination of $CF_3CF_2CH_3$ or $CF_3CHFCH_2F$, and of HFC-1234ze (mixture of E- and Z-isomers) by a catalytic vapor phase dehydrofluorination of $CF_3CH_2CHF_2$. U.S. Patent Publication No. 2007/0197842 discloses the production of HFC-1234yf by a catalytic vapor phase dehydrohalogenation of $CF_3CFClCH_3$ over a catalyst of activated carbon, Pd on C, Pt on C or Ni mesh. U.S. Patent Publication No. 2009/0030247 discloses the production of HFC-1234yf by a catalytic vapor phase dehydrochlorination of $CF_3CFClCH_3$ over a catalyst of CsCl and $MgF_2$.

There is a continuing need for more selective and efficient manufacturing processes for the production of HFC-1234yf

SUMMARY

In one aspect, disclosed is a process for the manufacture of 2,3,3,3-tetrafluoropropene comprising: contacting 1,1,1,2, tetrafluoro-2-chloropropane with a catalyst comprised of chromium (III) oxide, and at least 1% of an alkali metal, to produce a product mixture comprising 2,3,3,3-tetrafluoropropene; and recovering said 2,3,3,3-tetrafluoropropene from the product mixture produced.

The foregoing general description and the following detailed description are exemplary and explanatory only and are not restrictive of the invention, as defined in the appended claims.

DETAILED DESCRIPTION

In one aspect, disclosed is a process for the manufacture of 2,3,3,3-tetrafluoropropene comprising: contacting 1,1,1,2, tetrafluoro-2-chloropropane with a catalyst comprised of chromium (III) oxide, and at least 1% of an alkali metal, to produce a product mixture comprising 2,3,3,3-tetrafluoropropene; and recovering said 2,3,3,3-tetrafluoropropene from the product mixture produced.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Before addressing details of embodiments described below, some terms are defined or clarified.

The catalytic dehydrohalogenation of hydrofluorocarbons or hydrofluorochlorocarbonsto produce hydrofluoroolefins is ordinarily carried out in the vapor phase using a dehydrohalogenation catalyst. Vapor phase dehydrohalogenation catalysts are well known in the art. These catalysts include, but are not limited to, alumina, aluminum fluoride, fluorided alumina, metal compounds on aluminum fluoride, metal compounds on fluorided alumina; chromium oxides, fluorided chromium oxides, and cubic chromium trifluoride; oxides, fluorides, and oxyfluorides of magnesium, zinc and mixtures of magnesium and zinc and/or aluminum; lanthanum oxide and fluorided lanthanum oxide; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof. Catalysts for vapor phase dehydrochlorination include activated carbon, palladium on carbon, platinum on carbon, nickel mesh, and combinations of CsCl and magnesium fluoride.

In the preparation of HFC-1234yf by dehydrohalogenation of $CF_3CFClCH_3$, it is possible to obtain either HFC-1234yf or HCFC-1233xf, depending on whether dehydrochlorination or dehydrofluorination occurs.

It is possible to dehydrochlorinate $CF_3CClFCH_3$ (HFC-244bb) to HFC-1234yf with high selectivity and very little formation of HCFC-1233xf through competing dehydrofluorination, using a catalyst comprising chromium (III) oxide, and an alkali metal. Selectivity for the production of HFC-1234yf can be expressed as parts per hundred of the by-product relative to the amount of HFC-1234yf. By way of example, a product mixture formed from the dehydrochlorination of HFC-244bb comprising 60% HFC-1234yf and 20% HCFC-133xf would have 33 pph HCFC-1233xf. In one embodiment, the alkali metal is present in an amount of at least 1% by weight. In another embodiment, alkali metal is present in the catalyst in an amount of at least 1.5% by weight. In one embodiment, the alkali metal is selected from sodium, potassium, rubidium and cesium. In some embodiments, the catalyst further comprises boron.

In one embodiment, the catalyst comprises chromium (III) oxide, from 0.1% to 3% boron and at least 1000 ppm potassium. In another embodiment, the catalyst comprises chromium (III) oxide, from 0.5% to 2% boron and at least 1000 ppm potassium. In yet another embodiment, the catalyst comprises chromium (III) oxide, from 0.5% to 2% boron, and at least 2000 ppm potassium. In yet another embodiment, the catalyst comprises chromium (III) oxide and at least 1000 ppm potassium. In yet another embodiment, the catalyst comprises chromium (III) oxide and at least 1500 ppm potassium.

In one embodiment, the catalyst may be prepared by fusing a mixture of from 3 parts to 16 parts boric acid and 1 part potassium dichromate at from 500-800° C., cooling the mixture in air, crushing the solid to produce a powder, hydrolysis, filtering, drying, milling and screening. Numerous, examples of the preparation of Guignet's green can be found in the art, including U.S. Pat. No. 3,413,363, the disclosure of which is herein incorporated by reference.

In another embodiment, the catalyst may be prepared by doping Guignet's green chromium with additional potassium. In yet another embodiment, the catalyst may be prepared by doping chromium oxide with potassium.

The physical shape of the catalyst is not critical and may, for example, include pellets, powders or granules.

The reaction pressure can be subatmospheric, atmospheric or superatmostpheric. Generally, near atmospheric pressures are preferred. However, the dehydrofluorination can be beneficially run under reduced pressure (i.e., pressures less than one atmosphere).

In one embodiment, the catalytic dehydrofluorination is carried out in the presence of an inert gas such as nitrogen, helium, or argon. The addition of an inert gas can be used to increase the extent of dehydrofluorination. Of note are processes where the mole ratio of inert gas to hydrofluorocarbon undergoing dehydrofluorination is from about 5:1 to about 0.5:1. In one embodiment, nitrogen is the inert gas.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice and testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Example 1

Example 1 demonstrates the preparation of a chromium oxide catalyst doped with potassium.

In a 1000 ml Teflon® beaker, a solution of $KHCO_3$ (4.35 gm) in 200 ml of deionized water was combined with chromium oxide (Guignet's Green from Elementis Chromium). The slurry was allowed to stand at room temperature for one hour with occasional stirring. After evaporating to dryness, the resulting solid was crushed to a uniform powder and charged to a ceramic disk. It was heated to 400° C. over four hours and then kept at 400° in static air. The solid was weighed after cooling to room temperature and found to be 88.56 gm. The powder was pressed to 30,000 psi, and the resulting solid crushed and sieved to 12/20 mesh. The powder was analyzed by ICP and found to contain the following minor components: B, 1.92%; Ca, 3040 ppmw; Fe, 960 ppmw; K, 2.01%; Mg, 605 ppmw; Na, 4920 ppmw; Si, 41 ppmw; Sr, 25 ppmw.

Example 2

Example 2 demonstrates dehydrochlorination of 244bb over a doped chromium oxide catalyst prepared in Example 1.

An inconel tube (½ inch OD) was filled with 4 cc (5.03 gm) of the catalyst of Example 1. HFC-244bb was fed at 0.82 ml/hour through a vaporizer set at 40° C. using a $N_2$ sweep of 3.0 sccm giving us a total contact time of about 33 seconds while ramping the temperature up to 525° C. over 18 hours. No 245cb is detected.

TABLE 1

| Hours | 1234yf | 244bb | 1233xf | Furnace temp (C.) |
|---|---|---|---|---|
| 1 | 0.0 | 99.69 | 0.31 | 225 |
| 2 | 0.0 | 99.39 | 0.58 | 224 |
| 3 | 0.0 | 99.25 | 0.72 | 222 |
| 4 | 0.0 | 99.72 | 0.22 | 277 |
| 5 | 0.0 | 99.63 | 0.31 | 273 |
| 6 | 0.25 | 99.46 | 0.10 | 326 |
| 7 | 0.40 | 99.27 | 0.16 | 329 |
| 8 | 5.61 | 93.29 | 0.81 | 379 |
| 9 | 3.83 | 94.94 | 1.19 | 373 |
| 10 | 14.27 | 84.15 | 1.45 | 423 |
| 11 | 16.38 | 81.52 | 1.74 | 427 |
| 12 | 11.96 | 86.08 | 1.70 | 423 |
| 13 | 10.26 | 87.78 | 1.77 | 422 |
| 14 | 40.18 | 55.31 | 3.70 | 477 |
| 15 | 30.50 | 64.96 | 4.05 | 473 |
| 16 | 27.19 | 65.49 | 4.20 | 475 |
| 17 | 82.38 | 8.36 | 2.86 | 526 |
| 18 | 83.34 | 8.70 | 2.63 | 525 |

Example 3

Example 3 demonstrates dehydrochlorination of 244bb over a high potassium chromium oxide catalyst.

An inconel tube (½ inch OD) was filled with 4 cc (3.87 gm) of a commercial sample of Guignet's Green which is high in potassium. HFC-244bb was fed at 0.82 ml/hour through a vaporizer set at 40° C. using a $N_2$ sweep of 3.0 sccm giving us a total contact time of about 33 seconds while ramping the temperature up to 525° C. over 18 hours. No 245cb is detected. Results are indicated in the table below in mole percents.

TABLE 2

| Hours | 1234yf | 254eb | 244bb | 1233xf | Furnace temp (C.) |
|---|---|---|---|---|---|
| 1 | 14.20 | 0.07 | 82.76 | 2.40 | 224 |
| 2 | 2.25 | 0.00 | 96.59 | 1.16 | 220 |
| 3 | 2.08 | 0.00 | 96.76 | 1.16 | 223 |
| 4 | 7.39 | 0.10 | 90.51 | 1.88 | 277 |
| 5 | 5.29 | 0.08 | 92.55 | 2.00 | 281 |
| 6 | 11.69 | 1.04 | 81.99 | 4.81 | 326 |
| 7 | 5.90 | 0.62 | 88.69 | 4.65 | 323 |
| 8 | 7.62 | 5.99 | 74.44 | 11.23 | 378 |
| 9 | 5.21 | 4.28 | 76.96 | 12.79 | 373 |
| 10 | 5.19 | 2.22 | 79.59 | 11.56 | 422 |
| 15 | 22.98 | 0.56 | 70.99 | 4.90 | 476 |
| 16 | 27.10 | 0.31 | 70.07 | 2.33 | 476 |
| 17 | 32.33 | 0.30 | 65.45 | 1.70 | 526 |
| 18 | 48.54 | 0.53 | 48.83 | 1.75 | 526 |

A sample of this catalyst was analyzed by ICP and found to contain the following minor components: B, 1.6 wt %, K, 1.7 wt %, Ca, 50 ppm, Fe, 72 ppm, Na, 49 ppm, Si, 75 pm, Zr, 17 ppm.

Example 4

Example 4 demonstrates dehydrohalogenation of 244bb over an undoped commercial sample of Guignet's green.

An inconel tube (½ inch OD) was filled with 4 cc (3.32 gm) of undoped chromium oxide used in Example 1 above. HFC-244bb was fed at 0.82 ml/hour through a vaporizer set at 40° C. using a $N_2$ sweep of 3.0 sccm giving us a total contact time of about 33 seconds while ramping the temperature up to 525° C. over 24 hours.

TABLE 3

| Hours | 1234yf | 244bb | 1233xf | Furnace temp (C.) |
|---|---|---|---|---|
| 1 | 2.15 | 97.01 | 0.84 | 220 |
| 2 | 1.97 | 97.02 | 1.02 | 225 |
| 3 | 1.40 | 97.48 | 1.12 | 219 |
| 4 | 6.85 | 90.54 | 2.19 | 276 |
| 5 | 4.24 | 93.42 | 2.09 | 271 |
| 6 | 10.54 | 80.93 | 4.65 | 326 |
| 7 | 6.59 | 87.13 | 4.01 | 324 |
| 8 | 10.81 | 65.57 | 8.14 | 379 |
| 9 | 5.15 | 80.36 | 6.59 | 373 |
| 10 | 13.88 | 25.67 | 16.88 | 427 |
| 11 | 14.69 | 27.64 | 32.10 | 426 |
| 12 | 15.41 | 13.18 | 45.34 | 427 |
| 13 | 13.34 | 9.42 | 56.08 | 476 |
| 14 | 19.63 | 0.15 | 5.66 | 476 |
| 15 | 18.32 | 0.00 | 9.63 | 474 |
| 16 | 7.91 | 0.14 | 89.42 | 427 |
| 17 | 6.30 | 0.14 | 92.14 | 425 |
| 18 | 6.21 | 0.04 | 92.93 | 423 |
| 19 | 6.61 | 0.04 | 92.71 | 424 |
| 20 | 13.83 | 0.00 | 85.14 | 475 |
| 21 | 6.03 | 0.00 | 92.70 | 474 |
| 22 | 5.46 | 0.00 | 93.21 | 477 |
| 23 | 7.45 | 0.15 | 87.62 | 527 |
| 24 | 7.01 | 0.22 | 86.33 | 525 |

A sample of this catalyst was analyzed by ICP and found to contain the following minor components: B, 1.6 wt %, K, 150 ppm, Ca, 2800 ppm, Fe, 820 ppm, Na, 4550 ppm, Si, 135 pm, Zr, <1 ppm.

Example 5

Example 5 demonstrates the dehydrochlorination of 2-chloro-1,1,1,2-tetrafluoropropane in the presence of an activated carbon catalyst.

An inconel tube (½ inch OD) was filled with 4 cc (1.99 gm) of acid washed PCB Polynesian coconut shell based carbon from Calgon (6-10 mesh). HFC-244bb was fed at 1.04 ml/hour through a vaporizer set at 40° C. using a $N_2$ sweep of 2.4 sccm ($4.0 \times 10^{-8}$ $m^3$) giving a total contact time of about 32 seconds while controlling the reactor temperature at 400° C.

The data in Table 4 show the performance of this process with an activated carbon catalyst to make HFO-1234yf via HCl elimination over the period of 15 hours of operation.

TABLE 4

| Hours | conversion of 244bb | selectivity 1234yf | selectivity 1233xf |
|---|---|---|---|
| 1 | 78% | 67% | 13% |
| 2 | 75% | 59% | 18% |
| 3 | 68% | 56% | 22% |
| 4 | 58% | 44% | 27% |
| 5 | 51% | 31% | 35% |
| 6 | 46% | 15% | 39% |
| 7 | 46% | 6% | 38% |
| 8 | 47% | 3% | 32% |
| 9 | 45% | 2% | 29% |
| 10 | 31% | 3% | 36% |
| 11 | 21% | 5% | 64% |
| 12 | 23% | 5% | 66% |
| 13 | 24% | 5% | 67% |
| 14 | 24% | 6% | 73% |
| 15 | 23% | 6% | 72% |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for the manufacture of 2,3,3,3-tetrafluoropropene comprising: (a) contacting 1,1,1,2,tetrafluoro-2-chloropropane with a catalyst comprised of chromium (III) oxide, and at least 1% of an alkali metal, to produce a product mixture comprising 2,3,3,3-tetrafluoropropene; and (b) recovering said 2,3,3,3-tetrafluoropropene from the product mixture produced in (a); wherein said product mixture comprises less than 15 parts per hundred of 2-chloro-3,3,3-trifluoropropene; wherein said catalyst comprises at least 1 percent by weight potassium.

2. The process of claim 1, wherein said contacting step takes place in a heated vessel, wherein the temperature set point is at least 400° C.

3. The process of claim 1, wherein said contacting step takes place in a heated vessel, wherein the temperature set point is at least 470° C.

4. The process of claim 1, wherein said product mixture comprises less than 10 parts per hundred of 2-chloro-3,3,3-trifluoropropene.

5. The process of claim 1, wherein said product mixture comprises less than 5 parts per hundred of 2-chloro-3-3-3-trifluoropropene.

6. The process of claim 1, wherein said catalyst comprises at least 1.5 percent by weight potassium.

7. The process of claim 1, wherein said catalyst comprises at least 1 percent by weight cesium.

* * * * *